United States Patent [19]

Bader et al.

[11] Patent Number: 5,611,238
[45] Date of Patent: Mar. 18, 1997

[54] APPARATUS AND METHOD FOR AUTOMATIC CHARGING OF A MACHINE FOR CHARACTERIZING MECHANICAL AND/OR GEOMETRICAL PROPERTIES OF STAPLE FIBER SAMPLES

[75] Inventors: Jochen Bader, Schwabmünchen; August Schneider, Grossaitingen; Erwin Stolarski, Wollishausen, all of Germany

[73] Assignee: Hoechst Trevira GmbH & Co. KG

[21] Appl. No.: 543,123

[22] Filed: Oct. 13, 1995

[30] Foreign Application Priority Data

Oct. 17, 1994 [DE] Germany .......................... 44 37 026.1

[51] Int. Cl.⁶ .................................................. G01L 5/04
[52] U.S. Cl. ................................................... 73/160
[58] Field of Search .......................... 73/160, 789, 831, 73/833; 348/88

[56] References Cited

U.S. PATENT DOCUMENTS

| | | |
|---|---|---|
| 4,057,358 | 11/1977 | Young . |
| 4,270,252 | 6/1981 | Harrison et al. . |
| 4,392,384 | 7/1983 | Yquel . |
| 4,761,075 | 8/1988 | Matsushita et al. . |
| 5,351,308 | 9/1994 | Kaminer et al. . |

FOREIGN PATENT DOCUMENTS

| | | |
|---|---|---|
| 1573849 | 3/1970 | Germany . |
| 1648802 | 5/1971 | Germany . |
| 1183898 | 12/1983 | U.S.S.R. . |
| 601486 | 11/1949 | United Kingdom ..................... 73/160 |
| 1124307 | 8/1968 | United Kingdom . |
| WO922001 | 2/1992 | WIPO . |

OTHER PUBLICATIONS

20907 Tow crimp analyzer, No date.

*Primary Examiner*—Robert Raevis
*Attorney, Agent, or Firm*—Connolly & Hutz

[57] ABSTRACT

An apparatus and a method automatically charge a machine for characterizing mechanical and/or geometrical properties of staple fiber samples. The apparatus includes a plurality of clamping strips each having a plurality of clamps for receiving fiber samples, at least one reservoir for the clamping strips, and a transporter whereby the clamping strips or individual fiber samples are automatically brought from the reservoir into the machine. The method includes charging a plurality of clamping strips with fiber samples, introducing the charged clamping strips into a reservoir, and automatically bringing the individual clamping strips or individual fiber samples via a transporter from the reservoir into the machine.

22 Claims, 2 Drawing Sheets

APPARATUS AND METHOD FOR AUTOMATIC CHARGING OF A MACHINE FOR CHARACTERIZING MECHANICAL AND/OR GEOMETRICAL PROPERTIES OF STAPLE FIBER SAMPLES

The present invention relates to a magazine for fiber samples which permits the automatic charging of a machine for characterizing mechanical and/or geometrical properties of staple fiber samples, in particular crimp properties, and to a method for the automatic charging of such a machine using this magazine.

Methods for characterizing mechanical and/or geometrical properties of fibers, as for determining the crimp properties of fibers, are known per se.

One of the ways of characterizing the crimp properties of fibers is based on determining the crimp contraction. For this, the fiber is twice loaded with forces of a predetermined size, the first force being sufficiently small as not to cause crimp removal, and the second force being such that the crimp contraction is completely removed but the fiber is not stretched in the longitudinal direction. The difference in length between the crimp-contracted state and the extended state of the fiber in percent is known as the crimp contraction value. Measuring methods of this type are described for example in DE-A-2,925,810.

Such measurements are commonly carried out using the crimp balance. This is an apparatus in which a staple fiber to be characterized is clamped in at both ends, one of the clamps being attached to one end of the weighing beam. The other end of the weighing beam has an apparatus for receiving a mass. This mass creates the force which is necessary for removing the crimp from the in-test fiber in a defined manner.

The second clamp is movable in the fiber axis by means of a motor drive and sits on the shaft of a micrometer screw. The movable clamp is displaced to extend the fiber until the tensile force absorbed by the fiber equals the force created by the mass at the other end of the beam.

The balance is thus at equilibrium, which is detected photoelectrically and utilized, by means of an appropriate electronic system, to stop the clamp movement.

The change in length AL of the fiber corresponding to the distance the clamp has traveled can be read off on the micrometer screw.

Optical measurements for determining the crimp properties have already been disclosed. For instance, SU-A-1, 183,898 describes an optical determination of the stress-strain characteristics of crimped individual fibers. U.S. Pat. No. 4,057,350 discloses a method for determining the crimp of fiber tows by using the scattering of a laser beam as a measure of the degree of crimp. Further optical methods of measuring the crimp of running fiber tows are known from WO-A-92-2,001, U.S. Pat. No. 4,270,252 and RD-209,007. DE-C-1,473,750 describes the monitoring of the uniformity of the crimp of fiber tows by means of a mechanical method.

It is also known to characterize the crimp of fibers by determining the number of crimp arcs per unit length of the fiber at a predetermined fiber tension. This is usually done by means of the crimp balance and the number of crimp arcs of the clamped fibers is evaluated visually. The known method is not suitable for automation; moreover, it is personnel- and consequently cost-intensive.

DE-A-1,648,802 discloses a means for the automatic supply of samples to a tensile tester for textile fibers and the like. The sample carrier of this means has a plate-like construction.

DE-A-3,137,713 discloses a measuring apparatus with self-actuated charging and an automatic operating cycle for carrying out tensile tests on fibers. This measuring apparatus is equipped with a magazine which holds fiber samples adhered into tensioning pieces. These tensioning pieces are transferred into the measuring apparatus together with the fiber samples for measurement.

A further development of the above-described automated method of measurement is disclosed in DE-C-3,829,197 which permits simplified sample preparation and also the use of commercially available testers not adapted for measuring individual fibers. According to said reference, individual fibers are joined together to form an endless thread which is then subjected to a test method.

A further automated method for characterizing mechanical and/or geometrical properties of staple fibers and also an apparatus for carrying it out are described in unpublished German Patent Application P 43 43 157.7.

The present invention relates to an apparatus and a method whereby the degree of automation of the characterization of mechanical and/or geometrical properties of fiber samples can be increased once more.

The present invention relates to an apparatus for the automatic charging of a machine (1) for characterizing mechanical and/or geometrical properties of staple fiber samples, comprising the following elements:

A) a plurality of clamping strips (2) which each comprise a plurality of clamps (3) for receiving fiber samples (4), B) at least one reservoir means (5) for the clamping strips (2), and C) a transporter (6) whereby the clamping strips (2) or individual fiber samples (4) are automatically brought from the reservoir means (5) into the machine (1).

The fixing of the fiber samples (4) on the clamping strips (2) can be effected in any desired manner, for example by means of mechanical methods, as with springs or with counterweights, or with pneumatically or hydraulically operated clamps, or with magnetically, such as permanent- or electro-magnetically, operated clamps.

The clamping strips can be firmly positioned or preferably movable in the reservoir means (5).

Particularly preferably, the clamping strips (2) are horizontally movable in the reservoir means (5). The horizontal movement of the clamping strips (2) in the reservoir means (5) can be effected for example by chain drive or by pneumatically or hydraulically driven pistons.

In a particularly preferred embodiment, the reservoir means (5) comprises a plurality of mutually parallel, in particular two, transport belts (10) which each circulate between at least two rollers or pairs of rollers (11, 12) of which at least one roller or pair of rollers effects the driving of the relevant transport belt (10).

In a further particularly preferred embodiment, the clamping strips (2) comprise magnetic, preferably ferromagnetic, material, if appropriate in combination with nonmagnetic material, and the transport belts (10) have arranged on them a plurality of magnets (13), for example permanent magnets or electromagnets, whereby the clamping strips (2) can be fixed on the transport belts (10).

The clamping strips (2) can be removed from the reservoir means (5) by a transporter (6). The transporter (6) can move into the respective position of the clamping strips (2) in the reservoir means (5); preferably, however, the reservoir means (5) comprises a transfer position (14) at which the clamping strips (2) are transferred from the transporter (6).

Instead of the clamping strips (2) it is also possible for the transporting means (6) to remove individual fiber samples (4) from the clamping strips (2) situated in the reservoir means (5).

In a further preferred embodiment, the apparatus of the present invention comprises sensor means (15) which make it possible to determine the position of the clamping strips (2) in the reservoir means (5).

Examples of sensor means are light barriers, cameras, microswitches or in particular proximity switches.

The transporter (6) for the clamping strips (2) or the fiber samples (4) can be any apparatus suitable for this purpose. Examples are grippers, spindle drives, movable carriages or robot arms.

Particularly preferably the transporter is a hydraulically or preferably pneumatically operated carrier (16), in particular a gripper (16a) which is preferably operated pneumatically.

To transport into the machine (1) individual fiber samples (4) from the clamping strips (2) present in the reservoir means (5), the transporter (6) preferably has a pneumatically operated individual fiber clamp which is moved by means of the gripper (16a). The transport between clamping strip (2) and machine (1) can be effected for example by means of linear guidance or pivoting arm.

In a preferred embodiment of the apparatus of the present invention, the machine (1) comprises a receiver (17) into which a clamping strip (2) intended for measurement is deposited by means of the transporter (6).

This receiver (17) preferably comprises one or more abutments (19) for positioning the clamping strip (2).

The receiver (17) can in turn be positioned in the machine (1) and thus permits fine adjustment of the measuring position of clamping strip (2). This positioning is preferably effected by vertical and horizontal movement of the receiver (17), the vertical movement bringing about a coarse setting of the measuring position.

Particularly preferably, the receiver (17) is moved in the vertical direction by means of spindle drive (18).

In a further preferred embodiment of the present invention, the machine (1) and the apparatus for automatically charging the machine (1) are surrounded by a housing (30). This is a simple way of avoiding air movements which can have an adverse effect on the performance of the measurement.

The present invention also relates to a method for automatically charging a machine (1) for characterizing mechanical and/or geometrical properties of staple fiber samples, comprising the following measures:

a) charging a plurality of clamping strips (2) which each have a plurality of clamps (3) for receiving fiber samples (4) with fiber samples (4), b) introducing the charged clamping strips (2) into reservoir means (5), and c) automatically bringing the individual clamping strips (2) or individual fiber samples (4) by means of a transporter (6) from the reservoir means (5) into the machine (1).

For sample preparation, the clamping strips (2) are usually charged with fiber samples (4) by hand.

The clamping strips (2) charged with fiber samples (4) are then introduced into the reservoir means (5) by hand.

In a preferred embodiment, clamping strips (2) are introduced into the reservoir means (5), which comprises a plurality of mutually parallel, in particular two, transport belts (10), by placement onto the transport belts (10).

In a particularly preferred embodiment of the method of the present invention, the transport belts (10) charged with clamping strips (2) are moved by circulation of the transport belts and under monitoring by sensor means (15) into an initial position, the first of the clamping strips (2) intended for measurement being moved into a predetermined transfer position (14).

In a particularly preferred embodiment of the method of the present invention, the transport belts (10) charged with clamping strips (2), by circulation of the transport belts and under monitoring by sensor means (15), and the individual clamping strips (2) intended for measurement are moved into a predetermined transfer position (14), a carrier (16) is positioned above the clamping strip (2) situated in the transfer position (14), and, by lowering, gripping, raising, transport away in the horizontal direction and placement on a receiver (17) present in a starting position (22), the clamping strip (2) intended for measurement is transferred from the transfer position (14) into the machine (1); or, by lowering, gripping, raising, transport away in the horizontal direction and placement into the clamps of the machine (1), the individual fiber sample (4) intended for measurement is transferred from the transfer position (14) into the machine (1).

In a further preferred embodiment of the method of the present invention, the clamping strip (2) intended for measurement and placed on the receiver (17) is brought by lowering of the receiver (17) from a starting position (22) to a handover position (21), which is predetermined according to height, and then the measurement is carried out in machine (1) of the individual fiber samples (4) present in the clamping strip (2), the individual measuring operations being preceded by bringing the fiber samples (4) in each case into a defined measuring position (20) by a horizontal movement of the receiver (17).

The clamps (3) of clamping strip (2) which are occupied by fiber samples (4) are moved a predetermined distance by a transporter, so that an individual fiber sample (4) is brought into measuring position (20) of machine (1) for characterizing the mechanical and/or geometrical properties. For this purpose, the clamp (3) is positioned in the vicinity of the upper clamping jaw of machine (1) by means of an adjuster.

From the measuring position (20) the fiber sample (4) can be transferred into the machine (1) for characterizing the mechanical and/or geometrical properties. For this purpose, the machine (1) can have an upper clamp and optionally a lower clamp for attaching the fiber sample (4) to be characterized. The upper clamp is movable and the clamping strip (2) has been positioned by means of the receiver (17) in such a way that the clamps (3) of the clamping strip (2) are movable past in the vicinity of the upper clamp of the machine (1).

Subsequently the upper clamp of the machine (1) for characterizing the mechanical and/or geometrical properties is moved by means of a transporter, the upper clamp being present in the open position; on reaching the fiber sample (4), the upper clamp of the machine (1) for characterizing the mechanical and/or geometrical properties is closed by means of an opening and closing apparatus with the fiber sample (4) being transferred from the clamping strip (2).

Thereafter the upper clamp of the machine (1) for characterizing the mechanical and/or geometrical properties is moved by means of the transporter together with the fiber sample (4) into the machine (1) for characterizing the mechanical and/or geometrical properties of the fiber samples (4).

The machine (1) for characterizing the mechanical and/or geometrical properties makes it possible to characterize fiber samples of all kinds. These fiber samples can be uncrimped, but are in particular crimped fiber samples.

Examples of the characterization of mechanical properties are the recording of stress-strain diagrams, the measurement of the shrinkage, the shrinkage force, the crimp, the individual fiber fineness or a combination thereof.

A preferred example of the characterization of the geometrical properties is the determination of the number of crimp arcs of staple fibers.

As regards the individual fiber linear density and the fiber-forming material, the apparatus and method of the present invention are not subject to any restrictions.

Typical individual fiber linear densities range from 1 to 20 dtex.

Typical fiber-forming materials are polyphenylene sulfide, polyether ketone, glass or carbonized polyacrylonitrile (carbon fibers), polyacrylonitrile, polyamides, including the aramids, and polyesters, in particular polyethylene terephthalate.

An example of the characterization of the mechanical and/or geometrical properties of the fiber samples (4) using the machine (1) will now be described. This example concerns the automatic determination of the number of crimp arcs per unit length of crimped staple fibers.

According to this example, the number of crimp arcs per unit length of the staple fiber sample is determined in the following way using machine (1):

i) creating an image of predetermined length and predetermined width of the staple fiber sample by means of an imager which is movable in the direction of the longitudinal fiber axis, ii) creating from the image a digital grid whose pixels are deposited in the form of numerical values in a memory, said numerical values representing measurements of the lightness at the respective locus of the image, and iii) determining from the digital grid the number of crimp arcs in the depicted staple fiber sample by means of digital image processing.

The above-outlined method can be carried out by means of an imager which serves to create an image of predetermined length and predetermined width of the staple fiber sample present in machine (1) and which is movable in the direction of the longitudinal fiber axis, said imager driving a data processor which creates from the image a digital grid whose pixels are deposited in the form of numerical values in the memory.

The number of crimp arcs per unit length can be determined using the following procedure:

iv) creating in the image a longitudinal fiber axis which corresponds to the course which the staple fiber sample would have in the extended state, v) creating in the image a mid-line which extends within the longitudinal fiber axis of step iv) or parallel thereto at a predetermined distance and which intersects the staple fiber sample image created in step i) at least more than once, and vi) determining the number of intersections between the mid-line created in step v) and the staple fiber sample image created in step i) as a measure of the number of crimp arcs in the staple fiber sample appearing in the image.

The imager can be a line camera, for example.

After characterization, the upper clamp of machine (1) is opened by means of the opening and closing apparatus and the fiber sample (4) is removed from machine (1) for characterizing the mechanical and/or geometrical properties.

After characterization of the fiber samples (4) present in the clamping strip (2), the receiver (17) is moved into the starting position (22) together with the clamping strip (2) in a preferred embodiment of the method of the present invention, the clamping strip (2), by means of the carrier (16) present above the receiver (17), is brought into the reservoir means (5) by lowering this carrier (16), gripping, raising, transport away in the horizontal direction and placement of the clamping strip (2) into the transfer position (14) of the transport belts (10), and the transport belts (10) charged with clamping strips (2) are, by circulation of the transport belts and under monitoring by sensor means (15), moved on by a predetermined distance, so that the next clamping strip (2) intended for measurement moves up into the transfer position (14).

Thereafter the transporter (6) can accept the next clamping strip (2) and introduce it according to the above-outlined scheme into the machine (1) for characterizing the mechanical and/or geometrical properties.

The accompanying drawings illustrate the invention.

Figure 1:
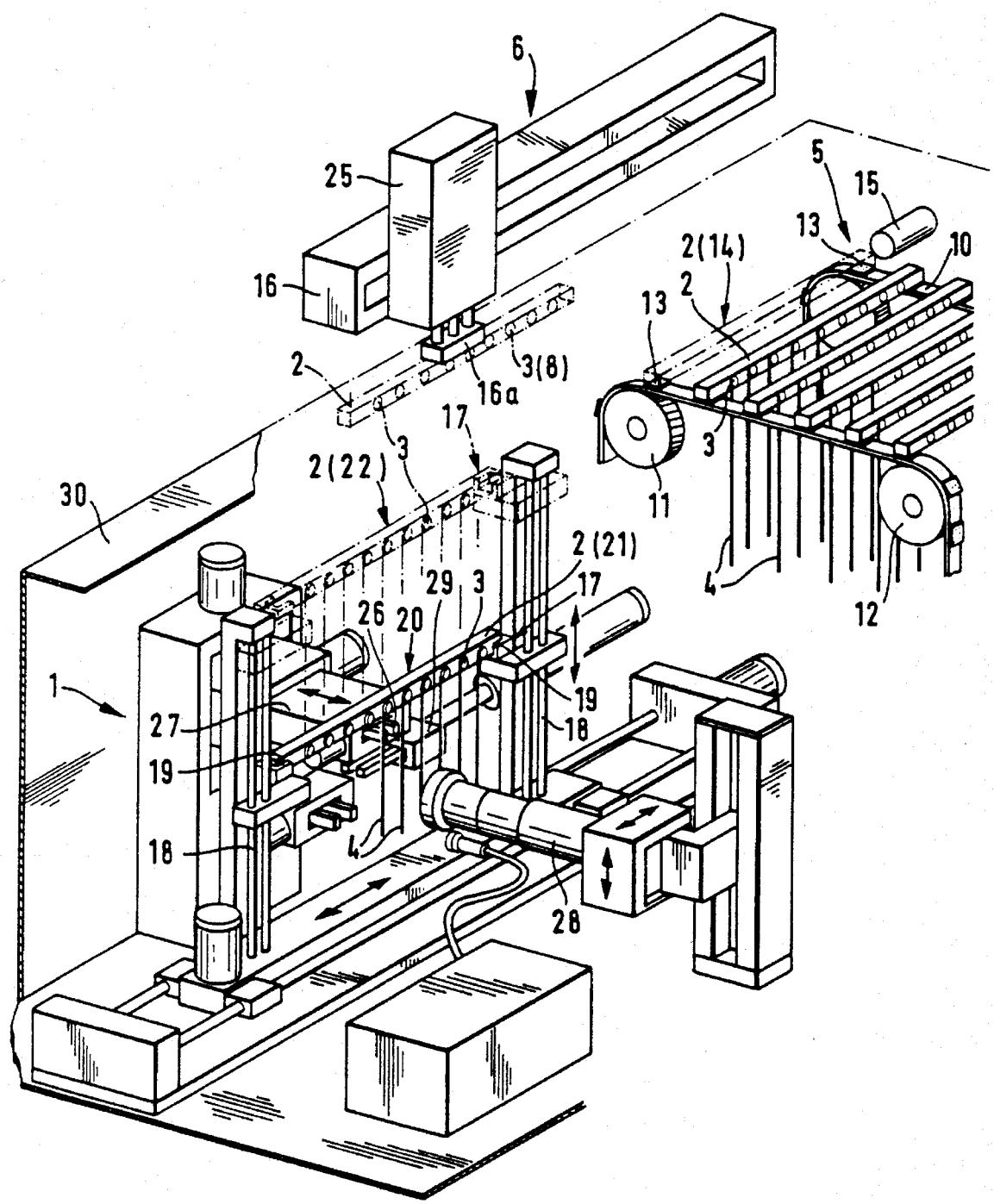
FIG. 1 shows a perspectival depiction of the cooperation of reservoir means, transporter and machine for characterizing the mechanical and/or geometrical properties.

FIG. 1 depicts a reservoir means (5) in cooperation with a transporter (6) and the machine (1) for characterizing mechanical and/or geometrical properties In the depicted apparatus, two transport belts (10) which are charged with clamping strips (2) and extend parallel to each other and which form the reservoir means (5) are moved by circulation of the transport belts and under monitoring by sensor means (15) into a transfer position (14). The clamping strips (2) contain the fiber samples (4) intended for measurement. The transport belts (10) circulate between two rollers (11, 12) which both drive the transport belts. The clamping strips (2) are fixed on the transport belts (10) by means of magnets (13). From the transfer position (14), the clamping strip (2) in question is transferred by means of a pneumatically operated gripper (16a), which represents the transporter (6), from the reservoir means (5) into the machine (1) for characterizing mechanical and/or geometrical properties. Gripper (16a) is moved by a carriage (25).

The pneumatically operated gripper (16a) puts down the clamping strip (2) in a receiver (17) present in a starting position (22). In the depicted embodiment, the receiver (17) is equipped with an abutment (19) for positioning the clamping strip (2).

The receiver (17) can be moved in the vertical direction and thus adapted to the sample length. For this, the receiver (17) is lowered from the starting position (22) to a height-predetermined handover position (21). This is effected in the depicted apparatus by means of a spindle drive (18). Horizontal advancement of the receiver (17) moves the samples in succession into the engagement region of the sample clamp (26). The individual fiber samples (4) are transferred for measurement from the clamping strip (2) into the sample clamp (26) which can be moved in the horizontal direction by means of carriage (27). The fiber sample is imaged by means of camera (28). Also provided is a disposal gripper (29) with which the fiber sample (4) can be removed from machine (1) after measurement; instead of the disposal gripper the fiber sample can also be removed by aspiration.

Following measurement of the fiber samples (4) present in the clamping strip (2) the above-outlined procedure takes place in the reverse order; that is, the receiver (17) is moved into the starting position (22) together with the clamping strip (2), the clamping strip (2), by means of the pneumatically operated gripper (16a) present above the receiver (17), is then brought into the reservoir means (5) by lowering this gripper, gripping, raising, transport away in the horizontal direction and placement of the clamping strip (2) into the transfer position (14) of the transport belts (10); then the transport belts (10) charged with clamping strips (2) are, by circulation of the transport belts and under monitoring by sensor means (15), moved on by a predetermined distance, so that the next clamping strip (2) intended for measurement moves up into the transfer position (14).

Figure 2:
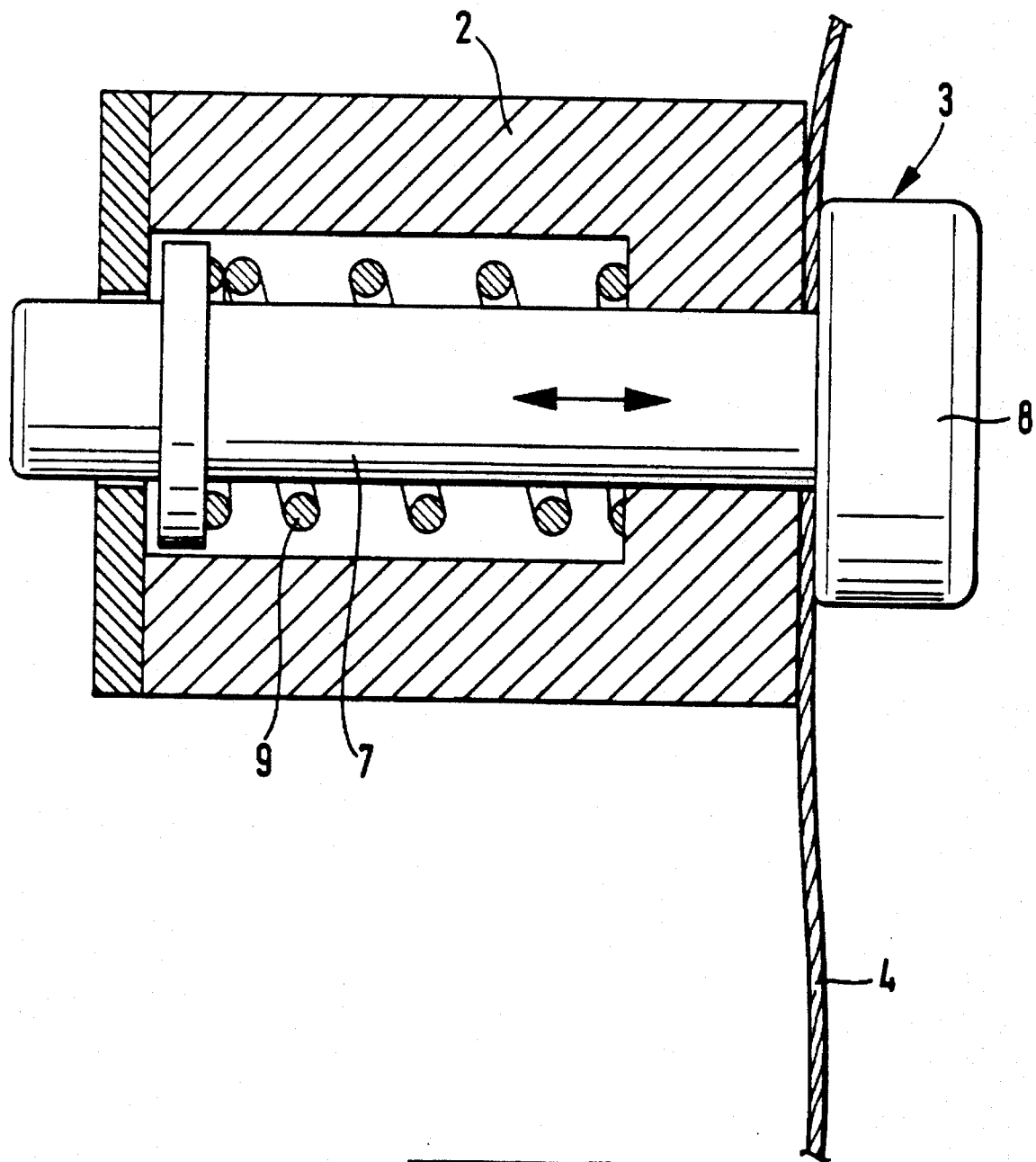
FIG. 2 depicts a particularly preferred embodiment of the clamping strip (2).

FIG. 2 depicts a particularly preferred embodiment of a clamping strip (2). In it, the clamps (3) are formed by clamping bolts (7) which extend in the transverse direction through the clamping strip (2) and are movable in this transverse direction and have on one side a broadened head (8) which is forced by a spring (9) mounted on the inside of the clamping strip against the clamping strip (2). This embodiment is notable for simple handling, robust construction and inexpensive fabrication.

What is claimed is:

1. Apparatus for the automatic charging of a machine for characterizing mechanical and/or geometrical properties of staple fiber samples, comprising the following elements:

A) a plurality of clamping strips which each comprise a plurality of clamps for receiving fiber samples, B) at least one reservoir means for the clamping strips, and C) a transporter whereby the clamping strips or individual fiber samples are automatically brought from the reservoir means into the machine.

2. The apparatus of claim 1, wherein the clamps are formed by clamping bolts which extend in a transverse direction through the clamping strip and are movable in this transverse direction and have on one side a broadened head which is forced by a spring mounted on the inside of the clamping strip against the clamping strip.

3. The apparatus of claim 1, wherein the clamping strips are horizontally movable in the reservoir means.

4. The apparatus of claim 3, wherein the reservoir means comprises a plurality of mutually parallel transport belts which each circulate between at least two rollers of which at least one roller effects driving of the relevant transport belt.

5. The apparatus of claim 4, wherein the clamping strips comprise magnetic material and the transport belts have arranged on them a plurality of magnets whereby the clamping strips can be fixed on the transport belts.

6. The apparatus of claim 3, wherein the reservoir means comprises a transfer position at which the clamping strips or individual fiber samples are transferred to the transporter.

7. The apparatus of claim 1, comprising sensor means which make it possible to determine the position of the clamping strips in the reservoir means.

8. The apparatus of claim 7, wherein the sensor means are proximity switches.

9. The apparatus of claim 1, wherein the transporter is a hydraulically operated gripper carrier.

10. The apparatus of claim 9, wherein the gripper carrier comprises a pneumatically operated individual fiber clamp.

11. The apparatus of claim 1, wherein the machine comprises a receiver into which a clamping strip is deposited by means of the transporter.

12. The apparatus of claim 11, wherein the receiver is movable in a vertical direction by means of a spindle drive.

13. The apparatus of claim 11, wherein the receiver comprises abutments for positioning the clamping strip.

14. The apparatus of claim 11, wherein the receiver is movable in a horizontal direction.

15. The apparatus of claim 1, housed together with the machine in a housing.

16. A method for automatically charging a machine for characterizing mechanical and/or geometrical properties of staple fiber samples, comprising the following measures:

a) charging a plurality of clamping strips which each have a plurality of clamps for receiving fiber samples with fiber samples, b) introducing the charged clamping strips into reservoir means, and c) automatically bringing the individual clamping strips or individual fiber samples by means of a transporter from the reservoir means into the machine.

17. The method of claim 16, wherein the clamping strips charged with fiber samples are introduced manually into a reservoir means, which comprises a plurality of mutually parallel transport belts which each circulate between at least two rollers of which at least one roller effects driving of the relevant transport belt, the clamping strips being laid onto the transport belts.

18. The method of claim 17, wherein the transport belts charged with clamping strips are moved by circulation of the transport belts and under monitoring by sensor means into an initial position, the first of the clamping strips intended for measurement being moved into a predetermined transfer position.

19. The method of claim 17, wherein the transport belts charged with clamping strips, by circulation of the transport belts and under monitoring by sensor means, and the individual clamping strips intended for measurement are moved into a predetermined transfer position, a carrier is positioned above the clamping strip situated in the transfer position, and, by lowering, gripping, raising, transport away in a horizontal direction and placement on a receiver present in a starting position, the clamping strip intended for measurement is transferred from the transfer position into the machine.

20. The method of claim 19, wherein the clamping strip intended for measurement and placed on the receiver is brought by lowering of the receiver to a measuring position, which is predetermined according to height, and then the measurement is carried out in the machine of the individual fiber samples present in the clamping strip, the individual measuring operations being preceded by bringing the fiber samples in each case into a defined measuring position by a horizontal movement of the receiver.

21. The method of claim 20, wherein, after the measurement of the fiber samples present in the clamping strip, the receiver is moved into the starting position, the clamping strip, by means of the carrier present above the receiver, is brought into the reservoir means by lowering this carrier, gripping, raising, transport away in a horizontal direction and placement of the clamping strip into the transfer position of the transport belts, and the transport belts charged with clamping strips are, by circulation of the transport belts and under monitoring by sensor means, moved on by a predetermined distance, so that the next clamping strip intended for measurement moves up into the transfer position.

22. The method of claim 17, wherein the transport belts charged with clamping strips, by circulation of the transport belts and under monitoring by sensor means, and the individual clamping strips intended for measurement are moved into a predetermined transfer position, a carrier is positioned above the clamping strip situated in the transfer position, and, by lowering, gripping, raising, transport away in the horizontal direction and placement into the clamps of machine, the individual fiber sample intended for measurement is transferred from the transfer position into the machine.

* * * * *